(12) United States Patent
Wang et al.

(10) Patent No.: US 8,288,573 B2
(45) Date of Patent: Oct. 16, 2012

(54) PROCESS FOR PREPARING A BIO-DIESEL

(75) Inventors: Haijing Wang, Beijing (CN); Zexue Du, Beijing (CN); Enze Min, Beijing (CN); Guoqiang Gao, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 361 days.

(21) Appl. No.: 12/519,314

(22) PCT Filed: Dec. 15, 2006

(86) PCT No.: PCT/CN2006/003429
§ 371 (c)(1),
(2), (4) Date: Aug. 25, 2009

(87) PCT Pub. No.: WO2008/071040
PCT Pub. Date: Jun. 19, 2008

(65) Prior Publication Data
US 2010/0087670 A1  Apr. 8, 2010

(51) Int. Cl.
*C11C 3/00* (2006.01)
*C10L 1/18* (2006.01)

(52) U.S. Cl. ........ 554/169; 554/165; 554/166; 554/167; 554/168; 554/170; 44/308; 44/307; 560/129

(58) Field of Classification Search .................. None
See application file for complete search history.

(56) References Cited

U.S. PATENT DOCUMENTS

| | | | |
|---|---|---|---|
| 4,652,406 A | 3/1987 | Lepper et al. | |
| 4,668,439 A * | 5/1987 | Billenstein et al. | 554/167 |
| 5,017,294 A * | 5/1991 | Durrieu | 210/708 |
| 5,525,126 A | 6/1996 | Basu et al. | |
| 6,090,959 A * | 7/2000 | Hirano et al. | 554/169 |
| 6,288,251 B1 * | 9/2001 | Tsuto et al. | 554/169 |
| 6,812,359 B2 * | 11/2004 | Goto et al. | 554/170 |
| 6,818,026 B2 * | 11/2004 | Tateno et al. | 44/385 |
| 2004/0087809 A1 | 5/2004 | Nakayama et al. | |

FOREIGN PATENT DOCUMENTS

| | | |
|---|---|---|
| CN | 1152885 A | 6/1997 |
| CN | 1247221 A | 3/2000 |
| CN | 1287572 A | 3/2001 |
| CN | 1111591 C | 6/2003 |
| CN | 1472280 A | 2/2004 |
| CN | 1473907 A | 2/2004 |
| CN | 1142993 C | 3/2004 |
| CN | 1664072 A | 9/2005 |
| CN | 1786117 A | 6/2006 |
| CN | 1810932 A | 8/2006 |
| DE | 3444893 A1 | 6/1986 |
| EP | 1477551 A1 | 11/2004 |

OTHER PUBLICATIONS

Warabi, Y. et al., Biodiesel fuel form vegetable oil by various supercritical alcohols, 2004, Applied Biochemistry and Biotechnology, vol. 113-116, pp. 793-801.*
English-language abstract of European Patent Application No. EP 0 985 654 A1 dated Mar. 15, 2000.
English-language abstract of Japanese Patent Application No. 2000-108379A dated Apr. 18, 2000.
English-language abstract of International Patent Application Publication No. WO 9600119 A1 dated Apr. 1, 2006.

* cited by examiner

*Primary Examiner* — Yate K Cutliff
(74) *Attorney, Agent, or Firm* — Scully, Scott, Murphy & Presser, P.C.

(57) ABSTRACT

The present invention provides a process for preparing a bio-diesel, comprising, in the presence of an alkaline metal compound, reacting an oil-fat with $C_1$-$C_6$ monohydric alcohol in a reactor at a reaction temperature of from 130 to 280° C. and a reaction pressure of from 1 to 12 MPa, separating fatty acid esters from the reacted materials, so as to produce the bio-diesel, wherein said alkaline metal compound is present in an amount of 0.001-0.07 wt %, in terms of the metal thereof, relative to the weight of the oil-fat. The process provided in the present invention has the advantages of great throughput and high yield of the bio-diesel.

21 Claims, No Drawings

PROCESS FOR PREPARING A BIO-DIESEL

TECHNICAL FIELD

The present invention relates to a process for preparing a bio-diesel by reacting an oil-fat with a monohydric alcohol.

BACKGROUND OF THE INVENTION

Bio-diesel may be prepared by transesterification of an oil-fat with a monohydric alcohol. Besides fatty acid esters, the products of the transesterification may include monoglycerides, diglycerides, glycerol by-products, as well as the unreacted alcohols and crude oil-fat. Bio-diesel primarily comprises fatty acid esters, and possibly other trace substances such as monoglycerides, diglycerides, glycerol and the like.

In the prior art, there are the acid catalysis method, base catalysis method, enzyme catalysis method and supercritical method for the preparation of bio-diesel.

CN1473907A discloses using as raw materials the heels from the refining of vegetable oils and the edible recovered oil, carrying out the production procedures comprising removing impurities by acidification, continuously dehydrating, esterifying, stratifying, and distilling under reduced pressure, and the catalyst used in the process is formed by complex formulation of inorganic and organic acids such as sulfuric acid, hydrochloric acid, p-toluene sulfonic acid, dodecylbenzene sulfonic acid, naphthalene sulfonic acid and the like. The continuous vacuum dehydration is carried out to a water content of less than 0.2% at a pressure of 0.08-0.09 MPa and a temperature of 60-95° C. Additionally, the catalyst is added in an amount of 1-3% in the esterification step; the esterification temperature ranges from 60-80° C.; and the reaction lasts 6 hours. After reaction, the product is neutralized to remove the catalyst, then stratified to remove water, and distilled under reduced pressure to obtain a bio-diesel. Compared with a base catalysis, the problems of said acid catalysis include slow reaction rate, massive spent acids, and environmental pollution.

DE3444893 discloses a process, wherein an inorganic acid is used as the catalyst; free fatty acids and alcohols are esterified at normal pressure and a temperature of from 50-120° C.; oils are pre-esterified and transesterified in the presence of an alkali metal catalyst. However, the residual inorganic acid catalyst will be neutralized with the alkali, so as to increase the amount of the alkali metal catalyst. Moreover, the pre-esterification will lengthen the processing process, increase the equipment investment, greatly enhance the energy consumption and incur a great loss of the materials. Moreover, the basic catalyst needs to be removed from the product, and a great deal of waste water will be produced.

CN1472280A discloses a process for preparing a bio-diesel, wherein fatty acid esters are used as the acyl receptor, and organisms are catalyzed for interesterification in the presence of a bio-enzyme. However, the presence of an enzyme catalyst has the disadvantages of long reaction time, low efficiency, high enzyme price, and a high possibility of inactivation in high purity methanol.

CN1142993C discloses a process for preparing fatty acid esters by using an oil-fat and alcohol in the absence of a catalyst and under the condition that either of said oil-fat and alcohol is in a supercritical state. The process had a relatively low raw material processing capacity.

CN1111591C discloses a process for preparing fatty acid esters by continuously reacting an oil-fat with a monohydric alcohol at a temperature of 270 to 280° C. and a pressure of 11-12 Mpa. However, the yield of fatty acid methyl ester is only 55-60%.

From the prior art above, it can be found that there are the problems of lower yield of fatty acid esters and lower raw material processing capacity in the preparation of a bio-diesel by medium and high pressure methods.

SUMMARY OF THE INVENTION

The present invention relates to a process for preparing a bio-diesel, comprising the steps of, in the presence of an alkaline metal compound, reacting an oil-fat with $C_1$-$C_6$ monohydric alcohol in a reactor at a reaction temperature of from 130 to 280° C. and a reaction pressure of from 1 to 12 MPa, separating fatty acid esters from the reacted materials, so as to produce the bio-diesel, wherein said alkaline metal compound is present in an amount of 0.001-0.07 wt % (in terms of the metal thereof) relative to the weight of the oil-fat. Said process has the advantages of high raw material throughput and high bio-diesel yield.

DETAILED DESCRIPTION OF THE INVENTION

The present invention relates to a process for preparing a bio-diesel, comprising the steps of, in the presence of an alkaline metal compound, reacting an oil-fat with a $C_1$-$C_6$ monohydric alcohol in a reactor at a reaction temperature of from 130 to 280° C. and a reaction pressure of from 1 to 12 MPa, separating fatty acid esters from the reacted materials, so as to produce a bio-diesel, wherein said alkaline metal compound is present in an amount of 0.001-0.07 wt %, in terms of the metal thereof, relative to the weight of the oil-fat.

Said term oil-fat is generally known in the art and is a general designation of oils and fats. The primary components thereof are fatty acid triglycerides. Generally, an oil-fat in a liquid state at normal temperature is termed as oil, and an oil-fat in a solid or semi-solid state at normal temperature is termed as fat. Said oil-fat comprises vegetable oils and animal oils, and further oils from microorganisms, algae and the like, and even oils having a higher acid number, crude oils, waste oil-fat and degenerative oil-fat, and the like, wherein said crude oils are the oil-fat which is not refined or fails to satisfy the product standard after refinement. The refining process includes, but is not limited to, degumming, alkali refining, dephosphoration, decolorization, deodorization and the like. The oil-fat may also comprise unsaponifiable matters in a relatively high content. Examples of vegetable oils comprise, but are not limited to, soybean oil, rapeseed oil, peanut oil, sunflower seed oil, palm oil, cocoanut oil, and aliphatic group-containing substances from fruits, stems, leaves, limbs and roots derived from various agricultural crops and wild plants (including a tall oil produced during the paper making). Examples of animal oil-fat include, but are not limited to, lard oil, beef tallow, mutton tallow, fish oil and the like. Said oil-fat may be the mixture of two or more oil-fats, or the mixture of the oil-fats having lower transesterification activities and the oil-fats having higher acid number. In one embodiment, the oil-fat comprises palm oil. In another embodiment, the oil-fat is a waste oil-fat.

Said $C_1$-$C_6$ monohydric alcohol is a monohydric fatty alcohol having from 1 to 6 carbon atoms, which may be a saturated or unsaturated alcohol. Examples of the monohydric alcohol include, but are not limited to, methanol, ethanol, n-propanol, isopropanol, allyl alcohol, butanol such as n-butanol, isobutanol and the like, amyl alcohol such as n-amyl alcohol and the like. A single alcohol, or a mixture of two or more alcohols may be used. Said monohydric alcohol is preferably selected from methanol, ethanol and butanol, more preferably methanol and ethanol, especially methanol. The molar ratio of $C_1$-$C_6$ alcohol to the oil-fat may range from 3 to 60:1, preferably from 4 to 12:1.

Examples of said alkaline metal compound include, but are not limited to, one or more selected from the group consisting of hydroxides, alcoholates, oxides, carbonates, bicarbonates and $C_{12}$-$C_{24}$ fatty acid salts of the Groups IA and IIA elements in the periodic table, preferably one or more selected from the group consisting of $C_{12}$-$C_{24}$ fatty acid salts of the Groups IA and IIA elements in the periodic table, more preferably one or more selected from the group consisting of $C_{12}$-$C_{24}$ fatty acid salts of sodium and potassium. Said alkaline metal compound is present in an amount of 0.003-0.05 wt %, preferably 0.005-0.035 wt %, in terms of the metal thereof, relative to the weight of the oil-fat.

In the process of the present invention, a tubular reactor may be used. The reactor may be provided with the oil-fat and alcohols separately or after being pre-mixed. The materials may be preheated by a pre-heater before being fed into the reactor, or directly fed into the reactor. If the materials are directly fed into the reactor, the reaction functions as both a pre-heater and a reactor. If a pre-heater is used, the oil-fat and alcohol may be pre-heated respectively or pre-heated together after they are mixed. The reaction temperature ranges from 130 to 280° C., especially from 170 to 238° C., more preferably from 190-238° C.; the reaction pressure ranges from 1 to 12 MPa, especially from 2 to 8 MPa, more preferably from 3 to 7 Mpa; the liquid hourly space velocity of the oil-fat ranges from 0.1 to 20 $h^{-1}$, especially from 0.5 to 15 $h^{-1}$, more preferably from 1 to 10 $h^{-1}$.

In the process of the present invention, the separation of fatty acid esters comprises the steps of (A) separating the mixed ester phase (the primary ingredients thereof comprise the desired fatty acid esters of monohydric alcohols, monoglycerides, diglycerides and a part of monohydric alcohols) and the glycerol phase (the primary ingredients thereof comprise glycerol and the remaining monohydric alcohols) formed in the reacted materials, and subsequently evaporating monohydric alcohols respectively from said mixed ester phase and optionally from the glycerol phase, or evaporating monohydric alcohols from the reacted materials before separating the mixed ester phase and the glycerol phase formed in the reacted materials; and (B) distilling or rectifying the mixed ester phase processed in step (A), or water-washing the mixed ester phase processed in step (A) and separating the ester phase formed after washing from the aqueous phase and collecting said ester phase, to obtain high purity fatty acid esters, and optionally distilling the glycerol phase processed in step (A) to obtain glycerol.

In step (A) above, monohydric alcohols may be evaporated by rectification or flash distillation under the condition that the temperature at the column bottom is less than 150° C., and the pressure may be normal pressure or vacuum, or greater than one atmospheric pressure.

In step (A) above, the mixed ester phase and glycerol phase may be separated by deposition or via a fiber bundle separator. Rapid separation via a fiber bundle separator is preferred. Said fiber bundle separator consists of a separating cylinder and a receiving tank, wherein the separating cylinder is furnished with fiber bundles consisting of stainless steel wires. The mixture of the mixed ester phase and the glycerol phase firstly passes through the separating cylinder and then is fed into the receiving tank for stratification, so as to achieve the separation of the mixture. The separation is carried out at a temperature of from 20 to 200° C., preferably from 40 to 100° C., at a pressure of greater than one atmospheric pressure or at normal pressure, e.g. from 0.1 to 0.5 MPa, preferably from 0.1 to 0.3 MPa, and at a space velocity of from 0.1 to 25 $h^{-1}$, especially from 1 to 10 $h^{-1}$, more preferably from 1 to 5 $h^{-1}$. In order to achieve better phase separation effect, the reacted materials which are heavily emulsified generally need to stand overnight if the deposition method is used. A fiber bundle separator can achieve a good separation effect in a very short time, so as to greatly enhance the separation rate and production efficiency.

In one embodiment of step (B) above, the mixed ester phase processed in step (A) above is distilled or rectified to obtain high purity fatty acid esters, wherein the distillation or rectification of said mixed ester phase may be carried out in a rectification column under reduced pressure or via a film evaporator. The mixed ester phase obtained in step (A) is fed into the reduced pressure rectification column, wherein the column bottom pressure is less than 0.1 MPa, preferably less than 0.01 MPa, more preferably less than 0.001 MPa; reflux may not occur, or the reflux ratio is controlled to range from 0.01 to 10:1, preferably from 0.1 to 2:1. The temperature of the column bottom or film evaporator ranges from 100 to 300° C., preferably from 170 to 280° C., more preferably from 190 to 280° C. The optional distillation of the glycerol phase may be similarly carried out by rectification in a reduced pressure rectification column or via a film evaporator.

In another embodiment of step (B) above, the mixed ester phase processed in step (A) above is washed by water, and the ester phase formed after washing is separated from the aqueous phase and collected to obtain high purity fatty acid esters. The water to be added during the washing is from 10 to 100 wt %, preferably from 20 to 80 wt % relative to the weight of the mixed ester phase; the temperature of water ranges from 25 to 100° C., preferably from 40 to 80° C. Washing may be carried out once or more times. If the ester phase obtained in step (B) has a relatively high acid number, an alkaline substance may be added into washing water. One or more alkaline substances selected from the group consisting of sodium carbonate, sodium bicarbonate, potassium carbonate, potassium bicarbonate, sodium hydroxide and potassium hydroxide may be added in the form of an aqueous solution for alkaline washing, wherein the alkaline substance in the aqueous solution is in a concentration of from 5 to 40 wt %, preferably from 5 to 20 wt %. The washed mixture may be re-separated into the ester phase and the aqueous phase by deposition, preferably via a fiber bundle separator, at a temperature of from 20 to 150° C., preferably from 40 to 100° C., at a pressure of greater than one atmospheric pressure or at normal pressure, and at a space velocity of from 0.1 to 25 $h^{-1}$, especially from 1 to 10 $h^{-1}$, more preferably from 1 to 5 $h^{-1}$.

The process of the present invention may further comprise step (C): separating monoglycerides and diglycerides from the mixed ester phase residues (i.e. residual liquid in the column bottom) distilled or rectified in step (B) by using a secondary molecular rectification, or evaporating monoglycerides and diglycerides from the mixed ester phase residues distilled or rectified in step (B) by using a primary molecular rectification. The evaporated monoglycerides and/or diglycerides may be recycled as required to the reactor inlet for a second reaction. More specifically, if the fraction having a higher monoglyceride content is desired, a secondary molecular rectification may be used. The residual liquid obtained from step (B) in the column bottom is fed into the molecular rectification device. The monoglyceride fraction in a higher content may be obtained at a pressure of less than 5

Pa, preferably less than 3 Pa, more preferably less than or equal to 1 Pa, and at a heating surface temperature of from 170 to 220° C., preferably 180 to 200° C. The fraction having a higher monoglyceride content may be used as an oil lubricating additive, and the heavy fractions may be fed into the secondary molecular rectification. At the pressure above and at a heating surface temperature of from 200 to 290° C., preferably 220 to 250° C., diglycerides having a higher purity may be obtained. These monoglycerides and diglycerides can be recycled as raw materials to the reactor inlet for second reaction. If the monoglyceride fraction in a higher content is not necessary, monoglycerides and diglycerides may be directly evaporated by using a primary molecular rectification, and then recycled to the reactor inlet for second reaction. In addition, the heavy residue may be used as fuel. In order to achieve the object of separating more components, the continuous multistage (or multi-group) operation may be used for the molecular rectification.

The process of the present invention has a strong raw material-processing capability, a high yield and a high purity of fatty acid ester. In addition, the process of the present invention has a strong material adaptability. Even if the raw materials comprise non-refined oils having a very high acid number or the oil-fat containing non-saponifiable matters in a higher content, they can be directly processed without the multifarious pretreatment so as to reduce the energy consumption and equipment investment. In addition, the process of the present invention may effectively separate monoglycerides, diglycerides and organic matters in non-refined oils having a relatively high boiling point, and may enable the components in non-refined oils which can become fatty acid esters of monohydric alcohols to be utilized to a maximum extent.

The process of the present invention is advantageous to reducing the acid number of the product. In addition, the color of the reacted oils is not deepened as compared with the raw oil, and there is no coking in the reactor.

EXAMPLES

The following examples are used to further explain the present invention, but the present invention is not limited to these examples. The raw materials used below are commercially available or easily produced according to the common technology in the art.

The reaction conversion rate stated in the examples may be calculated from the oil-fat weight before and after reaction; the bio-diesel yield may be obtained from the ratio of the bio-diesel weight to the oil-fat weight; the purity of fatty acid methyl ester (or butyl ester) may be obtained from the ratio of the fatty acid methyl ester (or butyl ester) weight to the bio-diesel weight.

Example 1

Palm oil and methanol were fed into a preheater having a temperature of 160° C. in a rate of 600 g/h and 100 g/h respectively. 0.009 wt % NaOH (in terms of sodium) based on the weight of the oil-fat was added. The preheated materials were continuously fed into a tubular reactor, wherein the reaction temperature was 200° C.; the reaction pressure was 8 MPa; the oil liquid hourly space velocity was 1 $h^{-1}$. Chromatographic analysis shown the reaction conversion rate of 100 wt % was achieved. The crude product flowing out from the reactor was then fed into a flash column to remove methanol at a temperature of less than 150° C., and recycle and reuse the methanol. The residual materials were fed into a separator comprising fiber bundles, and an ester phase was separated out and fed into a vacuum rectification column under the conditions of a temperature of 52° C. and a liquid hourly space velocity of 5 $h^{-1}$. Under the conditions of a vacuum degree of 8 mmHg and a column bottom temperature of 255° C., a bio-diesel was then obtained at the top of the column without reflux, wherein the yield thereof was 97.9 wt %, and the fatty acid methyl ester had a purity of 99.2 wt %. The residual liquid in the column bottom was fed into the molecular rectification equipment to obtain a light fraction having a higher monoglyceride content at a residual pressure of 5 Pa and at a heating surface temperature of 190° C. The residual materials having a high boiling point were fed into the secondary molecular rectification to obtain a light fraction at a residual pressure of 2 Pa and at a heating surface temperature of 244±2° C., wherein said light fraction as the raw materials can be recycled to the reactor inlet for the second reaction. In the raw materials, the components which may become fatty acid methyl ester were almost converted to the desired product.

Comparison Example 1

A bio-diesel was prepared according to the process of Example 1. The difference thereof lay in that NaOH was not added into the oil-fat. After separation according to the same process of Example 1, the bio-diesel yield was 30.5 wt %.

Example 2

Palm oil and methanol were fed into a preheater having a temperature of 140° C. in a rate of 600 g/h and 100 g/h respectively. 0.007 wt % Potassium oleate (in terms of potassium) based on the weight of the oil-fat was added. The preheated materials were continuously fed into a tubular reactor, wherein the reaction temperature was 235° C.; the reaction pressure was 2.9 MPa; the oil liquid hourly space velocity was 1 $h^{-1}$. Chromatographic analysis shown the reaction conversion rate of 100 wt % was achieved. The crude product flowing out from the reactor was then fed into a flash column to remove methanol at a temperature of less than 150° C., and recycle and reuse the methanol. The residual materials were fed into a separator comprising fiber bundles, and an ester phase and a glycerol phase were continuously separated out at a temperature of 25° C. and a liquid hourly space velocity of 9 $h^{-1}$, and the mixed ester phase was fed into a film evaporator. At a vacuum degree of 10 mmHg and a temperature of 255° C., a bio-diesel was then evaporated, wherein the yield thereof was 90.3 wt % and the fatty acid methanol purity was 99.0 wt %. The residual liquid in the column bottom was recycled as the raw materials to the reactor inlet for the second reaction. In the raw materials, the components which may become fatty acid methyl ester were almost converted to the desired product.

Example 3

Waste oil-fat having an acid number of 92.5 mgKOH/g and methanol were fed into a preheater having a temperature of 140° C. in a rate of 600 g/h and 140 g/h respectively. 0.01 wt % KOH (in terms of potassium) based on the weight of the oil-fat was added. The preheated materials were continuously fed into a tubular reactor, wherein the reaction temperature was 272° C.; the reaction pressure was 8.5 MPa; the oil-fat liquid hourly space velocity was 1.2 $h^{-1}$. Chromatographic analysis shown the reaction conversion rate of 100 wt % was achieved.

The crude product flowing out from the reactor was depressurized, and stood for deposition to separate out the mixed ester phase and glycerol phase. Then said phases were fed into the respective flash columns. Methanol was respectively and continuously flash-evaporated at a temperature of less than 150° C. The mixed ester phase in which methanol was evaporated was fed into a vacuum rectification column. At a vacuum degree of 8 mmHg, a column bottom temperature of 255-260° C., and a reflux ratio of 1:1, a bio-diesel was then evaporated out at the top of the column, wherein the yield was 95 wt %, and the fatty acid methyl ester had a purity of 99.5 wt %. The residual liquid in the column bottom was fed into the molecular rectification device, and a light fraction was evaporated out at a residual pressure of 1 Pa and a heating surface temperature of 250° C. Said light fraction may be recycled as the raw materials to the reactor inlet and be mixed with fresh materials for further reaction. In the raw materials, the components which may become fatty acid methyl ester were almost converted to the desired product.

A second reaction could also be carried out for the crude product, wherein the conditions of the second reaction were the same as those stated above. After the second reaction, the acid number of the ester phase was reduced to 1.2 mgKOH/g; the color of the product was not deepened as compared with the raw oils. In addition, there was no coking in the reactor.

Example 4

Rapeseed oils containing 5 wt % of non-saponifiable matter and methanol were fed into a preheater having a temperature of 160° C. in a rate of 600 g/h and 111 g/h respectively. 0.006 wt % NaOH (in terms of sodium) based on the weight of the oil-fat was added. The preheated materials were continuously fed into a tubular reactor, wherein the reaction temperature was 235° C.; the reaction pressure was 6 MPa; the oil liquid hourly space velocity was 3 $h^{-1}$. Chromatographic analysis shown the reaction conversion rate of 100 wt % was achieved. The crude product flowing out from the reactor was depressurized and then fed into a flash column to remove methanol at a temperature of less than 150° C., and recycle and reuse the methanol. The residual materials stood for deposition to separate out the ester phase and glycerol phase. The ester phase was vacuum-distilled. At a vacuum degree of 7 mmHg and a column bottom temperature of 240° C., a bio-diesel was then evaporated at the top of the column, wherein the yield thereof was 94 wt %, and the fatty acid methyl ester had a purity of 99 wt %.

Example 5

Refined soybean oil and methanol were fed into a preheater having a temperature of 200° C. in a rate of 600 g/h and 100 g/h respectively. 0.006 wt % NaOH (based on the weight of the oil-fat, and in terms of sodium) was added into the reaction system. The preheated materials were continuously fed into a tubular reactor, wherein the reaction temperature was 260° C.; the reaction pressure was 8 MPa; the oil liquid hourly space velocity was 1.2 $h^{-1}$. Chromatographic analysis shown the reaction conversion rate of 100 wt % was achieved. The crude product flowing out from the reactor was depressurized to 0.1-0.13 MPa, and the liquid was fed into the fiber bundle separator. At a temperature of 40° C. and a liquid hourly space velocity of 10 $h^{-1}$, an ester phase and a glycerol phase were separated out and fed into the respective flash column so as to respectively flash-evaporate methanol. The ester phase in which methanol was evaporated had an acid number of 1.4 mgKOH/g and a glycerol content of 0.24 wt %. 5% potassium carbonate solution having a temperature of 40° C. was added into the ester phase for washing. After washing, the mixture was then fed into the fiber bundle separator. At a temperature of 40° C. and a liquid hourly space velocity of 10 $h^{-1}$, an ester phase and an aqueous phase were separated out, wherein the ester phase had an acid number of 0.25 mgKOH/g. The bio-diesel yield was 96 wt %, wherein the fatty acid methyl ester had a purity of 98.5 wt %; and the free glycerol was in a content of 0.015 wt %.

Example 6

Lard oil as the raw material was continuously fed at a butanol/oil molar ratio of 9 into a preheater having a temperature of 160° C. 0.018 wt % NaOH (in terms of sodium) based on the weight of the oil-fat was added. The preheated materials were continuously fed into a tubular reactor, wherein the reaction temperature was 235° C.; the reaction pressure was 6 MPa; the oil-fat liquid hourly space velocity was 1.1 $h^{-1}$. The crude product flowing out from the reactor was depressurized and fed into a flash column to remove and recycle butanol at a temperature of less than 150° C. and recycled. The residual materials stood for deposition and were separated into an ester phase and a glycerol phase. The ester phase was vacuum-distilled. At a vacuum degree of 7 mmHg and a column bottom temperature of 240° C., a bio-diesel was then evaporated at the top of the column, wherein the yield was 67 wt %, and the fatty acid butyl ester had a purity of 98 wt %.

Example 7

Soybean oil as the raw material was continuously fed at a methanol/oil molar ratio of 5 and an oil liquid hourly space velocity of 6 $h^{-1}$ into a tubular reactor. 0.006 wt % NaOH (in terms of sodium) based on the weight of the oil-fat was added, wherein the reaction temperature was 272° C.; the reaction pressure was 8 MPa; the oil-fat reaction conversion ratio was 100 wt %. Methanol and glycerol were separated from the reaction crude product according to the steps as stated in Example 4, and the ester phase was vacuum-distilled. A bio-diesel was then evaporated at the top of the column, wherein the yield was 94 wt %, and the fatty acid methyl ester had a purity of 99.3 wt %.

The residual liquid at the bottom of the rectification column comprised fatty acid methyl esters, monoglycerides and diglycerides. Moreover, said liquid could be recycled as the raw materials to the reactor inlet for reuse prior to being mixed with fresh materials.

What is claimed is:

1. A process for preparing a bio-diesel, comprising the steps of, in the presence of an alkaline metal compound, reacting an oil-fat with a $C_1$-$C_6$ monohydric alcohol selected from methanol, ethanol, n-propanol, allyl alcohol, n-butanol, amyl alcohol, and hexanol, in a tubular reactor at a reaction temperature of from 130 to 238° C. and a reaction pressure of from 1 to 12 MPa, separating fatty acid esters from the reacted materials, so as to produce a bio-diesel, wherein said alkaline metal compound is present in an amount of 0.001 to less than 0.02875 wt %, in terms of the metal thereof, relative to the weight of the oil-fat.

2. The process according to claim 1, characterized in that said oil-fat comprises palm oil.

3. The process according to claim 1, characterized in that said oil-fat is a waste oil-fat.

4. The process according to claim 1, characterized in that said monohydric alcohol is methanol, ethanol or n-butanol.

5. The process according to claim 1, characterized in that said alkaline metal compound is one or more selected from the group consisting of hydroxides, alcoholates, oxides, carbonates, bicarbonates and $C_{12}$-$C_{24}$ fatty acid salts of the Groups IA and IIA elements in the periodic table.

6. The process according to claim 1, characterized in that said alkaline metal compound is one or more selected from the group consisting of $C_{12}$-$C_{24}$ fatty acid salts of the Groups IA and IIA elements in the periodic table.

7. The process according to claim 1, characterized in that said alkaline metal compound is one or more selected from the group consisting of $C_{12}$-$C_{24}$ fatty acid salts of sodium and potassium.

8. The process according to claim 1, characterized in that said alkaline metal compound is present in an amount of 0.003-0.018 wt %, in terms of the metal thereof, relative to the weight of the oil-fat.

9. The process according to claim 1, characterized in that the reaction temperature ranges from 170 to 238° C.

10. The process according to claim 1, characterized in that the reaction pressure ranges from 2 to 8 MPa.

11. The process according to claim 1, characterized in that the reaction pressure ranges from 3 to 7 MPa.

12. The process according to claim 1, characterized in that $C_1$-$C_6$ alcohol and oil-fat are in a molar ratio of 3-60:1.

13. The process according to claim 1, characterized in that $C_1$-$C_6$ alcohol and oil-fat are in a molar ratio of 4-12:1.

14. The process according to claim 1, characterized in that the oil-fat has a liquid hourly space velocity of 0.1-20 $h^{-1}$.

15. The process according to claim 1, characterized in that the oil-fat has a liquid hourly space velocity of 0.5-15 $h^{-1}$.

16. The process according to claim 1, characterized in that the separation of fatty acid esters comprises the steps of
   (A) separating the mixed ester phase and the glycerol phase formed in the reacted materials, and subsequently evaporating monohydric alcohols respectively from said mixed ester phase and optionally from the glycerol phase, or evaporating monohydric alcohols from the reacted materials before separating the mixed ester phase and the glycerol phase formed in the reacted materials;and
   (B) distilling or rectifying the mixed ester phase processed in step (A), or water-washing the mixed ester phase processed in step (A) and separating the ester phase formed after washing from the aqueous phase and collecting said ester phase, to obtain fatty acid esters, and optionally distilling the glycerol phase processed in step (A) to obtain glycerol.

17. The process according to claim 16, characterized in that the monohydric alcohol is evaporated in step (A) by flash distillation or rectification under the condition that the temperature at the column bottom is less than 150° C.

18. The process according to claim 16, characterized in that, in step (A), the separation between the mixed ester phase and the glycerol phase is carried out by deposition or via a fiber bundle separator.

19. The process according to claim 18, characterized in that said fiber bundle separator consists of a separating cylinder and a receiving tank, wherein the separating cylinder is furnished with fiber bundles consisting of stainless steel wires, and the separation between the mixed ester phase and the glycerol phase is carried out by passing them through the separating cylinder and then feeding into the receiving tank for stratification.

20. The process according to claim 16, characterized in that, during the washing process in step (B), an alkaline matter is added into the washing water.

21. The process according to claim 16, characterized in further comprising step (C): evaporating monoglycerides and diglycerides from the mixed ester phase residues distilled or rectified in step (B) by using a primary molecular rectification, or evaporating and separating monoglycerides and diglycerides from the mixed ester phase residues distilled or rectified in step (B) by using a secondary molecular rectification, with or without a second reaction.

* * * * *